United States Patent [19]

Bäbler

[11] Patent Number: 5,565,578

[45] Date of Patent: Oct. 15, 1996

[54] PROCESS FOR THE PREPARATION OF DIARYLDIKETOPYRROLOPYRROLE PIGMENTS

[75] Inventor: Fridolin Bäbler, Hockessin, Del.

[73] Assignee: Ciba-Geigy Corporation, Tarrytown, N.Y.

[21] Appl. No.: 586,499

[22] Filed: Jan. 16, 1996

Related U.S. Application Data

[63] Continuation of Ser. No. 321,493, Oct. 12, 1994, abandoned.

[51] Int. Cl.$^6$ .......................... C08K 5/00; C07D 487/08
[52] U.S. Cl. .......................... 548/453; 106/498; 106/506; 106/494; 106/485
[58] Field of Search .......................... 548/453; 106/498, 106/506, 494, 495

[56] References Cited

U.S. PATENT DOCUMENTS

| | | | |
|---|---|---|---|
| 4,415,685 | 11/1983 | Iqbal et al. | 524/92 |
| 4,579,949 | 4/1986 | Rochat et al. | 546/167 |
| 4,632,704 | 12/1986 | Bäbler | 106/288 |
| 4,659,775 | 4/1987 | Pfenninger et al. | 524/92 |
| 4,783,540 | 11/1988 | Bäbler | 548/453 |
| 4,791,204 | 12/1988 | Jost et al. | 548/101 |
| 4,810,304 | 3/1989 | Jaffe et al. | 106/494 |
| 5,286,863 | 2/1994 | Bäbler et al. | 546/56 |

FOREIGN PATENT DOCUMENTS

| | | |
|---|---|---|
| 55-07474 | 2/1980 | Japan . |
| 60-035055 | 2/1985 | Japan . |
| 60-032850 | 2/1985 | Japan . |
| 61-118460 | 6/1986 | Japan . |
| 61-185568 | 8/1986 | Japan . |
| 62-013464 | 1/1987 | Japan . |

OTHER PUBLICATIONS

Derwent Abstract: 85–084119[14] (1985).
Derw. Abst. (1989)—302204/42 of EP 337,435.

*Primary Examiner*—David B. Springer
*Attorney, Agent, or Firm*—George R. Dohmann

[57] ABSTRACT

A process for conditioning diaryldiketopyrrolo[3,4-c]pyrrole pigments (DPP) and for preparing solid solutions having a DPP component are disclosed. The inventive processes involve dissolving the DPP in aqueous, basic DMSO, alone, or in mixture with additional components in the case of a solid solution, and then precipitating the conditioned pigment or pigment solid solution by methods known in the art.

20 Claims, No Drawings

PROCESS FOR THE PREPARATION OF DIARYLDIKETOPYRROLOPYRROLE PIGMENTS

This application is a continuation of application Ser. No. 08/321,493 filed Oct. 12, 1994, now abandoned.

BRIEF DESCRIPTION

A process for preparing diaryldiketopyrrolo[3,4-c]pyrrole pigments and pigment solid solutions comprising a diaryldiketopyrrolo[3,4-c]pyrrole component by precipitation from basic dimethylsulfoxide.

BACKGROUND

The diaryldiketopyrrolo[3,4-c]pyrrole (DPP) pigments are an important class of pigments on the worldwide market due to their outstanding chroma and excellent heatfastness and weatherfasmess properties. The DPP pigments and their preparation are well-known in the art. In addition, DPP pigment solid solutions are also known in the art.

The present invention provides a new process for conditioning DPP pigments and the preparation of pigment solid solutions containing at least one DPP wherein the DPP is dissolved in the form of a salt in dimethylsulfoxide and then precipitated.

Known processes for conditioning the DPP pigments include various milling methods, such as wet milling, or milling in an alcohol in the presence of a base, and recrystallization in organic solvents. Known processes for preparing solid solutions containing a DPP include recrystallization in organic solvents, acid or alkaline precipitation and intensive milling of a mixture containing the corresponding pigment components.

The present process is distinguished from known processes in that it relates to precipitating the DPP pigment or solid solution from aqueous, basic dimethylsulfoxide (DMSO) and is based on the discovery that aqueous, basic DMSO is capable of dissolving DPP pigment salts in high concentrations at temperatures below about 80° C. Since DMSO is readily available and is one of the least toxic polar organic solvents, the present process is a simple, economical and particularly environmentally friendly process. The present process is additionally advantageous over the known processes because highly transparent, semitransparent and/or opaque pigments having outstanding performance properties are prepared simply by varying process parameters.

DETAILED DESCRIPTION

This invention relates to the surprising discovery that DPP pigment crudes are ideally conditioned by precipitation from aqueous, basic dimethylsulfoxide (DMSO). In particular, the present invention relates to a process for preparing a diaryldiketopyrrolo[3,4-c]pyrrole pigment, which comprises (a) preparing a pigment salt solution by dissolving a diaryldiketopyrrolo[3,4-c]pyrrole in dimethylsulfoxide which contains an effective salt-forming mount of a base and sufficient water to solubilize the base, (b) precipitating the diaryldiketopyrrolo[3,4-c]pyrrole from the pigment salt solution to form a pigment suspension, and (c) isolating the pigment. The expression "DPP pigment" includes both those pigments which consist of a single DPP compound or pigment solid solutions containing a DPP compound.

The process of this invention is particularly suitable for preparing diaryldiketopyrrolo[3,4-c]pyrrole pigments of the formula:

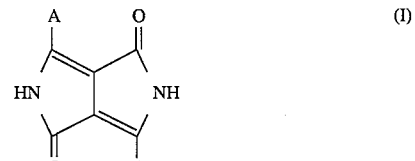

or

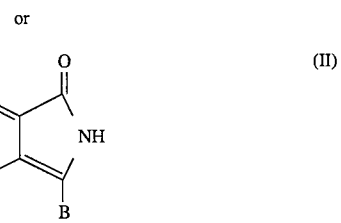

in which A and B are independently of each other a group of the formula

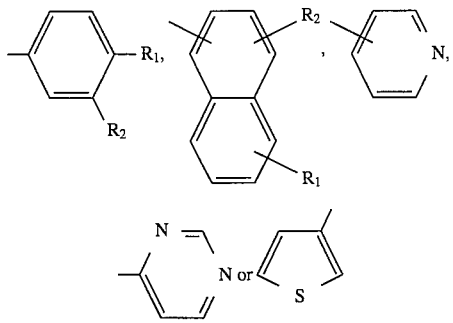

in which $R_1$ and $R_2$ are independently of each other hydrogen, halogen, $C_1$–$C_5$-alkyl, $C_1$–$C_5$-alkoxy, —$SR_3$,—$N(R_3)_2$, —$CF_3$,—CN or a group of the formula

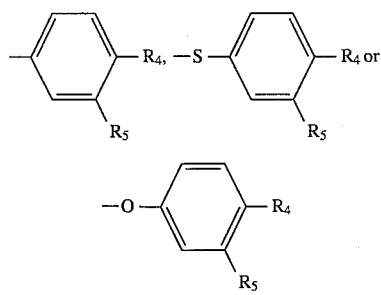

$R_3$ is $C_1$–$C_5$-alkyl and $R_4$ and $R_5$ are independently of each other hydrogen, halogen, $C_1$–$C_5$alkyl, $C_1$–$C_5$-alkoxy,—$SR_3$ or—CN.

Preferred diaryldiketopyrrolo[3,4-c]pyrroles are compounds of the Formula I in which both A substituents are identical groups of the formula

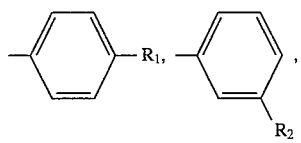

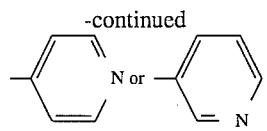

in which R₁ is hydrogen, chlorine, bromine, cyano, methyl, ethyl, tert.-butyl or phenyl and $R_2$ is hydrogen, chlorine, methyl, or cyano.

3,6-di(4-chlorophenyl)-1,4-diketopyrrolo[3,4-c]pyrrole, 3,6-di(4-tert-butylphenyl)-1,4-diketopyrrolo[3,4-c]pyrrole, 3,6-di(3-cyanophenyl)-1,4-diketopyrrolo[3,4-c]pyrrole, 3,6-di(4-biphenyl)-1,4-diketopyrrolo[3,4-c]pyrrole, 3,6-di(4-methylphenyl)-1,4-diketopyrrolo[3,4-c]pyrrole and 3,6-diphenyl-1,4-diketopyrrolo[3,4-c]pyrrole are DPPs that are especially suitable for the present conditioning process.

Generally, the DMSO contains an effective salt-forming amount of a base and sufficient water to solubilize the base.

In general, an effective salt-forming amount of base is the amount required to cause the DPP to be converted to a salt form in the aqueous, basic DMSO solvent. In particular, a base concentration of from about 2 to 6 moles of the base per mole of DPP is present in the aqueous, basic DMSO. Preferably, from 2 to 4 moles of the base per mole of DPP is used. Quaternary ammonium compounds and alkali metal hydroxides are suitable as the base. Preferably, the base is a alkali metal hydroxide, for example, sodium hydroxide or potassium hydroxide.

In general, the base is added to the DMSO in the form of an aqueous solution of the base. The presence of water is necessary for the base solubility in the DMSO. The amount of water required varies depending on the identity of the base. Thus, an effective amount of water is at least the amount required to solubilize sufficient base in the DMSO to convert the DPP to salt form. In general, the DMSO contains less than about 50 parts of water per 100 pans of DMSO, for example, from 10 to 40 pans of water per 100 parts of DMSO. Since the presence of water is necessary for base solubility, no water may be required, if, for example, a DMSO-soluble salt of the DPP is added directly to the DMSO to form a basic, DMSO solution of the DPP salt.

The DMSO is capable of dissolving DPPs in their salt form to form a pigment salt solution. In general, the DPP concentration in the pigment salt solution is above about 5 percent by weight Preferably, the concentration of the DPP represents from about 8 to 17 weight percent of the pigment salt solution.

In a preferred method, the pigment salt solution is prepared by mixing a DPP crude with aqueous, basic DMSO below 100° C., for example at room temperature or, preferably, from 40° to 70° C. The mixture is stirred, preferably below 100° C., most preferably at or below 80° C., until the pigment salts are completely dissolved.

The pigment is then precipitated from the pigment salt solution to form a pigment suspension by precipitation methods known in the art. For example, suitable precipitation methods include drowning into water or a $C_1$–$C_4$alkanol, or by adding $C_1$–$C_4$alkanol and/or water to the pigment salt solution. The presence of a mineral acid, such as hydrochloric, phosphoric or sulfuric acid, or an organic acid, such as acetic acid, in the water and/or $C_1$–$C_4$ alkanol is advantageous in such precipitation methods. The conditioned pigment is also precipitated by direct introduction of hydrogen chloride gas into the pigment salt solution.

Preferably, the pigment salt solution is drowned into water or a $C_1$–$C_4$alkanol or a $C_1$–$C_4$alkanol/water mixture. Suitable $C_1$–$C_4$alkanols include methanol, ethanol, n-propanol, isopropyl alcohol and tert-butanol; especially methanol and ethanol. Water, methanol or methanol/water mixtures are particularly suitable for drowning the pigment salt solution.

Depending on the pigment and on the drowning conditions, pigments with a particle size in the range from 0.005 microns to 3 microns are obtained. Thus, highly transparent pigments with an extremely small particle size (<0.051 μm), or opaque pigments with a large particle size (>0.21 μm), as well as pigments with an intermediate particle size, are produced by the present process.

In general, more opaque pigments are prepared when an alcohol is chosen as the precipitation medium and the resulting pigment suspension is stirred for from 1 to 24 hours or more at temperatures of 40° C. or higher.

Generally, more transparent pigments are prepared at lower temperatures using aqueous precipitation medium. For example, a transparent pigment is generally prepared when water or water/alcohol mixtures containing from 50 to 95 percent, preferably 70 to 90 percent, of water, and 5 to 50 percent, preferably 10 to 30 percent, of alcohol, or preferably water alone, is the precipitation medium and the temperature is about 40° C. or lower, preferably 5° to 35° C.

The particle size of the resulting transparent pigment is controlled by a particle ripening step wherein the pigment suspension is stirred for a period of from about 5 minutes to about 10 hours at a temperature of from about 15° C. to 35° C. prior to the isolation of the conditioned pigment.

A greater degree of particle size control, particularly for small particle size pigments, is exercised by adding particle growth inhibitors to the precipitation medium. Pigment particle growth inhibitors, also known as antiflocculating agents, are well-known in the art. Generally quinacridone or DPP derivatives, such as the sulfonic acid, phthalimidomethyl-, imidazolylmethyl-, pyrazolylmethyl-, N- (dialkylaminoalkyl)sulfonic acid amide derivatives are suitable pigment particle growth inhibitors. Such particle growth inhibitors may also act as crystal phase directors under certain conditions.

The particle growth inhibitors are added to the precipitation medium in amounts ranging from 0.05 to 15%, preferably 0.1 to 8%, and most preferably 0.5 to 5% based on the corresponding pigment, either before or after, preferably before, the precipitation of the DPP pigment. The particle growth inhibitors additionally serve to lessen or avoid flocculation, increase pigment dispersion stability, and positively affect rheological characteristics.

The pigment particle growth inhibitor is preferably a phthalimidomethylquinacridone, a pyrazolylmethylquinacridone, a quinacridone sulfonic acid, a diphenyl-diketopyrrolo [3,4-c]pyrrole sulfonic acid or the corresponding metal salts, for example, aluminum or calcium salts.

When the ripening of the pigment crystals is complete, the conditioned pigment is isolated by filtration, with the presscake being washed with water or an organic solvent, preferably methanol, followed by water and dried.

If the pigment salt solution contains a mixture of dissolved pigment salts that are capable of forming a solid solution, the present precipitation method is also a method of preparing solid solution pigments containing a DPP component; especially binary and ternary solid solutions containing a DPP component. Thus, the present invention also relates to a process as described above wherein the pigment salt solution comprises the diaryldiketopyrrolo[3,4-c]pyrrole and a second dissolved organic pigment which forms a solid solution with the diaryldiketopyrrolo[3,4-c] pyrrole upon precipitation.

Accordingly, the present invention also relates to a process for preparing a solid solution pigment comprising a diaryldiketopyrrolo[3,4-c]pyrrole, which process comprises (a) preparing a pigment salt solution by dissolving a diaryldiketopyrrolo[3,4-c]pyrrole and a second organic pigment in dimethylsulfoxide which contains an effective salt-forming amount of a base and sufficient water to solubilize the base;

(b) precipitating the solid solution from the pigment salt solution to form a solid solution pigment suspension; and (c) isolating the solid solution pigment.

All of the discussion above relating to the preparation of the pigment salt solution, the precipitation step and isolation and ripening of the DPP pigment applies equally to the present process for preparing a solid solution pigment The expression "solid solution" is used in this application to mean a pigment composition which has an x-ray diffraction pattern that is different from the sum of the x-ray diffraction patterns of the individual components. Thus, the expression solid solution includes the "guest-host" solid solutions, which have the x-ray pattern of one of the component pigments, and "solid compounds" or "mixed crystals", which have an x-ray pattern different from that of the individual components.

Solid solution pigments which are obtained according to this process contain a DPP component of formula (I) or (II) and as a further component one or more organic pigments capable of forming soluble pigment salts in basic DMSO and forming pigment solid solutions with the corresponding diaryldiketopyrrolo[3,4-c]pyrrole. Such solid solutions contain for example two or more diaryldiketopyrrolpyrrole components or one or more DPP components combined with a component from a different class of pigment, for example, the quinacridone pigments. Preferred solid solutions are binary or ternary solid solutions that contain two or three DPPs or one or two DPPs and a quinacridone component; especially binary solid solutions wherein the second organic pigment is a DPP or a linear quinacridone and ternary solid solutions containing two DPP components and a quinacridone component.

Thus, an embodiment of the present process is utilized to prepare pigment solid solutions which contain (a) at least one DPP of the formula I or II and (b) at least one linear quinacridone compound of the formula

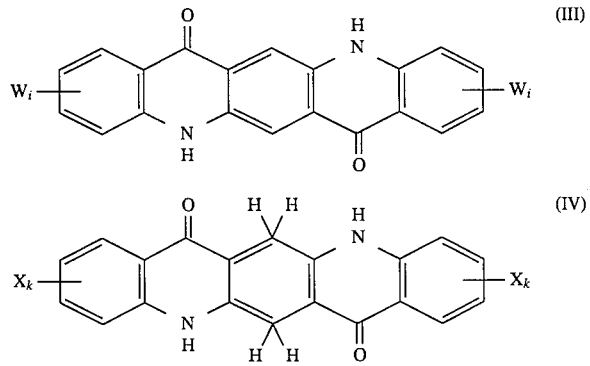

in which W and X are independently of one another halogen, $C_1$–$C_5$ alkyl or $C_1$–$C_5$ alkoxy and i and k are zero, 1 or 2.

The present process is especially suitable for preparing binary or ternary solid solutions wherein the diaryldiketopyrrolo[3,4-c]pyrrole is selected from the group consisting of 3,6-di(4-chlorophenyl)-1,4-diketopyrrolo-[3,4-cl-pyrrole, 3,6-di(4-tert-butylphenyl)- 1,4-diketopyrrolo[3,4-c]pyrrole, 3,6-di(3-cyanophenyl)-1,4-diketopyrrolo [3,4-c]pyrrole, 3,6-di(4-biphenyl)-1,4-diketopyrrolo-[3,4-c]-pyrrole, 3,6-di(4-methylphenyl)-1,4-diketopyrrolo-[3,4-c]-pyrrole and 3,6-diphenyl-1,4-diketopyrrolo- [3,4-c]-pyrrole and the second pigment is one or two different pigments selected from the group consisting of 3,6-di(4-chlorophenyl)-1,4-diketopyrrolo [3,4-c]pyrrole, 3,6-di(4-tert-butylphenyl)-1,4-diketopyrrolo[3,4-c]pyrrole, 3,6-di(3-cyanophenyl)-1,4-diketopyrrolo[3,4-c]pyrrole, 3,6-di(4-biphenyl)-1,4-diketopyrrolo [3,4-c]pyrrole, 3,6-di(4-methylphenyl)-1,4-diketopyrrolo[ 3,4-c]pyrrole 3,6-diphenyl-1,4-diketopyrrolo[3,4-c]pyrrole, quinacridone, 2,9-dichloroquinacridone, 2,9-dimethoxyquinacridone and 2,9-dimethylquinacridone.

It is known in the art that solvent suspensions of very small particle size pigments tend to filter extremely slowly. Surprisingly, the precipitated pigments according to this invention can be easily filtered and washed.

Depending on the DPP pigment or pigment solid solution, it can be advantageous to reslurry the aqueous pigment presscake in water or diluted acid like sulfuric acid or hydrochloric acid to improve the washing process and to assure a complete hydrolysis of the pigment salt.

Additionally, it can be advantageous to also add the above mentioned antiflocculating agent in the form of an aqueous presscake to the aqueous presscake of the DPP or pigment solid solution prior to drying in order to improve the pigment's rheological properties.

Depending on the end use, it can be advantageous to add specific amounts of texture improving agents to the pigment. Suitable texture improving agents are, in particular, fatty acids of not less than 18 carbon atoms, for example stearic or behenic acid or the amides or metal salts thereof, preferably calcium or magnesium salts, as well as plasticizers, waxes, resin acids such as abietic acid or metal salts thereof, colophonium, alkyl phenols or aliphatic alcohols such as stearyl alcohol or vicinal diols such as dodecane-1,2-diol, and also modified colophonium/—maleate resins or fumaric acid/colophonium resins or polymeric dispersants. The texture improving agents are preferably added in amount of 0.1 to 30%, by weight, most preferably 2 to 15% by weight, based on the final product.

The conditioned pigments and solid solution pigments prepared according to the present process are suitable for use as pigments for coloring high-molecular-weight organic materials. Examples of high-molecular-weight organic materials which may be colored or pigmented with the compositions of this invention are cellulose ethers and esters such as ethylcellulose, nitrocellulose, cellulose acetate, cellulose butyrate, natural resins or synthetic resins such as polymerization resins or condensation resins, for example aminoplasts, in particular urea/formaldehyde and melamine/formaldehyde resins, alkyd resins, acrylic resins, phenolic plastics, polycarbonates, polyolefins, polystyrene, polyvinyl chloride, polyamides, polyether, polyetherketone, polyurethanes, polyesters, rubber, casein, silicone and silicone resins, singly or as mixtures.

The above high-molecular-weight compounds may be used singly or as mixtures in the form of plastics, melts or of spinning solutions, varnishes, paints or printing inks. Depending on the end use, it is advantageous to use the pigments as toners or in the form of preparations. The compositions of the invention are preferably employed in an amount of 0.1 to 30% by weight based on the high molecular organic material to be pigmented.

Pigmentation of high-molecular-weight organic compounds with the pigments of the invention is carried out, for example, by incorporating such pigments, optionally in the form of a masterbatch, into the substrates using roller mills, mixing or grinding machines. The pigmented material is then brought into the desired final form by methods which are known per se, for example, calendering, molding, extruding, coating, spinning, casting, or by injection molding. It is often desirably to incorporate plasticizers into the high molecular compounds before processing in order to produce non-brittle moldings or to diminish their brittleness. Suitable plasticizers, are for example, esters of phosphoric acid, phthalic acid, or sebacic acid. The plasticizers may be incorporated before or after working the composition into the polymers. To obtain different shades, it is also possible to add fillers or other chromophoric components such as white, colored, or black pigments, in any amount, to the high-molecular-weight organic compounds, in addition to the compositions of this invention.

For pigmenting varnishes and printing inks, the high-molecular-weight organic materials and the pigments obtained according to the present invention, together with optional additives such as fillers, other pigments, siccatives, or plasticizers, are finely dispersed or dissolved in a common organic solvent or mixture of solvents. The procedure may be such that the individual components or blends thereof are dispersed or dissolved in the solvent and subsequently all the components are mixed.

The process according to this invention is simple, economic, and particularly environmentally friendly. The base and solvents can be recovered and reused from the flitrate.

A new trend in the automotive paint industry is the use of highly transparent organic pigments in combination with pearlescent pigments, such as $TiO_2$ and other metal oxide coated mica pigments for the creation of effect color paints. The transparent organic pigments and pigment solid solutions that are prepared according to the present process are particularly suitable for use in such effect color paints.

The process according to this invention is ideally suited for the preparation of highly transparent, highly saturated, weatherfast pigments for its use in solventborne or waterborne automotive paint systems.

Generally, the pigments obtained by the process of this invention are suitable for all pigment applications and are distinguished by excellent color strength, transparency or opacity, good fastness to light, weathering and heat, excellent purity and saturation, as well as by good dispersibility when incorporated into plastics or varnishes.

The following examples further illustrate the preferred embodiments of this invention. In these examples, all pans given are by weight unless otherwise noted.

EXAMPLE 1A

A 1 liter flask equipped with a thermometer, stirrer, and condenser is charged with 51.3 grams of 45% aqueous potassium hydroxide, 45 ml water, and 300 ml DMSO. 70 grams 3,6-di(4-chlorophenyl)-1,4-diketopyrrolo[3,4-c]pyrrole crude are added with stirring at 40°–50° C. The mixture is heated to 75° C. and stirred at 75°–80° C. for 10 minutes, whereby the DPP pigment dissolves completely in the form of its dipotassium salt. The resulting dark hot solution is drowned into 2 liter methanol at 18°–40° C. The pigment suspension is heated to reflux and stirred for three hours at reflux temperature. The bright red pigment is isolated by filtration and is washed DMSO-free with methanol followed by water to a pH 7.5–8.0 and dried. The pigmentary 3,6-di(4-chlorophenyl)-1,4-diketopyrrolo [3,4-c]pyrrole shows an opaque, highly saturated, red masstone and a strong red color in $TiO_2$ extension by rubout obtained according to ASTM method D-387-60 in a lithographic varnish.

EXAMPLE 1B

The procedure of Example 1A is repeated replacing the 45% aqueous potassium hydroxide with 33 grams of 50% aqueous sodium hydroxide. A saturated, opaque red DPP pigment with good pigment properties is obtained.

EXAMPLE 2

The procedure of Example 1A is repeated replacing the 3,6-di(4-chlorophenyl)-1,4-diketopyrrolo [3,4-c]pyrrole crude with 62 grams 3,6-di(4-methylphenyl)- 1,4-diketopyrrolo-[3,4-c]-pyrrole crude to yield an opaque highly saturated red pigment with good heat stability and high color strength when applied in plastics.

EXAMPLE 3

A 500 ml flask equipped with a stirrer, thermometer and condenser is charged with 110 ml DMSO, 10.8 grams of 45% aqueous potassium hydroxide and 10 ml water. 17.1 grams 3,6-di(4-biphenyl)-1,4-diketopyrrolo[3,4-c]pyrrole crude are added at 40°–50° C. The mixture is heated and stirred for 5 minutes at 70°–80° C. The resulting dark solution of the pigment salt is drowned into methanol at 20°–40° C. precipitating the pigment. The pigment suspension is stirred at reflux for 3 hours and then filtered. The presscake is washed with methanol, then water to a pH 7 to 7.5, followed by drying. The pulverized pigment shows a semitransparent bluish-red masstone and a very strong red color in $TiO_2$ extension by rubout obtained according to ASTM method D-387-60 in a lithographic varnish.

EXAMPLE 4

A 1 liter flask equipped with a thermometer, stirrer, and condenser is charged with 41.3 grams of 45% aqueous potassium hydroxide, 40 ml water, and 350 ml DMSO. Seventy grams 3,6-di(4-biphenyl)-1,4-diketopyrrolo[3,4-c]pyrrole crude are added under stirring at 40°–50° C. The mixture is heated to 80°–85° C. and stirred at 80°–85° C. for 10 miniutes. The resulting dark solution of the pigment salt is drowned into 2 liters of water at 18°–22° C. causing the pigment to precipitate and the temperature to rise to 40° C. The pigment suspension is stirred at 35°–40° C. for 2 hours. The pigment is filtered and washed with water to a pH 9. Despite the very small particle size of the precipitated pigment, the pigment suspension is easily filtered and washed. The aqueous pigment presscake is reslurried in 500 ml of 5% aqueous $H_2SO_4$ solution and stirred for 2 hours at room temperature. The pigment is isolated by filtration, followed by washing with water to a pH 6.5–7.0 and drying. The pigment shows a highly transparent, strongly saturated maroon color and excellent durability when applied in plastics or paints.

EXAMPLE 5

A 1 liter flask equipped with a thermometer, stirrer, and condenser is charged with 41.3 grams of 45% aqueous potassium hydroxide, 40 ml water, and 350 ml DMSO. Seventy grams 3,6-di(4- biphenyl)-1,4-diketopyrrolo[3,4-c] pyrrole crude are added under stirring at 40°–50° C. The mixture is stirred for 10 minutes at 55°–58° C. The resulting dark solution of the pigment salt is drowned into 2 liters of methanol at 24°–26° C. causing the DPP to precipitate and the temperature to rise to 36° C. The pigment suspension is stirred for one hour at 30°–36° C., then filtered, followed by washing to a pH 8.0–9.0. The pigment presscake is reslurried in 5% aqueous sulfuric acid solution and stirred at room temperature for two hours. The pigment is isolated by filtration, followed by washing with water to a pH 6.5–7.0 and dried. The pigment shows a highly transparent, strongly saturated maroon color with excellent weather and heat stability.

EXAMPLE 6

A 1 liter flask equipped with a thermometer, stirrer and condenser is charged with 73.3 grams of 45% aqueous potassium hydroxide, 60 ml water and 300 ml DMSO. 1.1 grams phthalimidomethylquinacridone as particle growth inhibitor and 70 grams 3,6-diphenyl-1,4-diketopyrrolo[3,4-c]pyrrole crude are added with stirring at 40°–50° C. The mixture is stirred for 5 minutes at 45°–55° C. The resulting dark solution of the pigment salt is drowned into 2 liters of water at 23° to 33° C. causing the pigment to precipitate. The pigment suspension is stirred for 5 minutes then filtered. The presscake is washed with water to a pH 7.5 to 8.5 and then dried to yield 69.5 grams of a reddish pigment powder. The pigment shows a highly transparent yellowish red color and excellent weatherability when applied in automotive paints.

EXAMPLE 7

A 1 liter flask equipped with a thermometer, stirrer, and condenser is charged with 94 grams of 45% of aqueous potassium hydroxide, 76 ml water, and 600 ml DMSO. 128.4 grams 3,6-di(4-chlorophenyl)-1,4-diketopyrrolo-[3,4-c]-pyrrole crude, and 2 grams phthalimidomethylquinacridone as particle growth inhibitor are added with stirring at 40°–60° C. The mixture is heated and stirred at 60°–63° C. for 5 minutes. The resulting hot, dark solution of the pigment salt is drowned into a mixture of 1.4 liter water with 600 ml methanol at 18°–22° C. causing the pigment to precipitate and the temperature to rise to 32°34° C. The pigment suspension is stirred at 30°–33° C. for one hour, then diluted with a mixture of 350 ml water and 150 ml methanol, stirred for 5 minutes, and filtered. The presscake is washed DMSO-free with water to a pH 7 to 8 and dried. The red pulverized pigment shows a highly transparent red masstone and a very strong red color in $TiO_2$ extension by rubout in a lithographic varnish obtained according to ASTM method D-387-60.

EXAMPLE 8

A 1 liter flask equipped with a thermometer, stirrer and condenser is charged with 73.3 grams of 45% potassium hydroxide, 60 ml water, and 300 ml DMSO. Seventy grams 3,6-di(4-chlorophenyl)-1,4-diketopyrrolo[3,4-c]pyrrole crude are added with stirring at 40°–50° C. The mixture is stirred for 5 minutes at 50°–55° C. The resulting dark solution of the pigment salt is drowned into 2 liters of water at 20°–23° C. causing the pigment to precipitate and the temperature to rise to 30°–33° C. The pigment suspension is stirred for 70 minutes at around 30° C. The pigment is isolated by filtration and is washed with water to a pH 7.5–8.0 and dried. Despite the very small pigment particle size generated during the precipitation process, the pigment suspension is easily filtered and washed at an acceptable timing rate. The dried, pulverized pigment shows a highly transparent, strong, highly saturated red color with excellent durability when applied in an automotive coating system.

EXAMPLE 9

The procedure of Example 8 is repeated replacing the 3,6-di(4-chlorophenyl)-1,4-diketopyrrolo[3,4-c]pyrrole crude with 3,6-di(3-cyanophenyl)-1,4-diketopyrrolo [3,4-c] pyrrole crude. A highly transparent orange pigment is obtained showing high gloss, high chroma, and excellent durability when applied in aqueous or solventborne ink systems.

EXAMPLE 10

A 500 ml flask equipped with a stirrer, thermometer, and condenser is charged with 100 ml DMSO, 8.9 grams of 45% aqueous potassium hydroxide, and 9 ml water. 8.5 grams unsubstituted gamma-II-quinacridone and 1.5 grams 3,6-diphenyl-1,4-diketopyrrolo[3,4-c]pyrrole are added at 40°–50° C. The mixture is heated and stirred for 5 minutes at 80°–90° C. The resulting deep blue solution of the pigment salts is drowned into methanol at 20°–40° C., causing the pigment to precipitate. The pigment suspension is stirred at reflux temperature for 1 hour, then filtered. The presscake is washed DMSO-free with methanol, followed by water to a pH 7.0–8.0, and then dried. The pulverized pigment shows the x-ray diffraction pattern of a gamma-1-quinacridone without peaks of the DPP pigment and different from the x-ray diffraction diagram of the gamma-II-quinacridone starting material. Thus, a quinacridone/DPP pigment solid solution with the quinacridone as host is formed. The pigment solid solution shows an opaque highly saturated strong red color when applied in plastics or paints with excellent weatherfastness properties.

EXAMPLE 11

A 1 liter flask equipped with a thermometer, stirred, and condenser is charged with 53.4 grams of 45% potassium hydroxide, 50 ml water, and 400 ml DMSO. 51 grams unsubstituted quinacridone pigment and 9 grams of 3,6-diphenyl-1,4-diketopyrrolo[3,4-c]-pyrrole crude are added under stirring at 40°–50° C. The mixture is heated to 80°–85° C. and stirred at 80°–85° C. for 5 minutes. The resulting dark violet blue solution of the pigment salt mixture is cooled to 30°–35° C. and then drowned into 1.5 liters of water at 20°–30° C., causing the pigment to precipitate. The pigment suspension is stirred for 5 minutes then filtered. The pigment presscake is washed with water to pH 7.5–8.5, then dried. The pulverized pigment shows a highly transparent, medium red shade when applied in an automotive paint system with excellent durability. The pigment shows the x-ray diffraction pattern with the main peaks of a small particle size gamma quinacridone pigment with no peaks detectable from the diaryldiketo-pyrrolo pyrrole pigment, demonstrating the formation of a pigment solid solution.

EXAMPLE 12

A 1 liter flask equipped with a thermometer, stirrer, and condenser is charged with 49.3 grams 45% of aqueous potassium hydroxide, 45 ml water, and 350 ml DMSO. 42 grams 2,9-dichloroquinacridone crude, 28 grams 3,6-di(4-chlorophenyl)-1,4-diketopyrrole[3,4-c]pyrrole crude and 1 gram of phthalimidomethylquinacridone are added with stirring at 40°–50° C. The mixture is heated and stirred for 5 minutes at 60°–65° C. The resulting dark violet solution of the pigment salt mixture is drowned into 2 liters of water having a temperature of 18° C., causing the pigment to precipitate and the temperature to rise to 30° C. The pigment suspension is stirred for one hour at 25°–30° C. and then filtered. The suspension filters fast. The presscake is washed with water until DMSO-free to pH 7.0–7.5, then dried. The electron micrograph of the pulverized pigment shows a very small particle size pigment with an average particle size of <0.05μm. The x-ray diffraction pattern shows mainly the peaks at the 2θ angles of a 2,9-dichloroquinacridone pigment. The pigment is highly transparent and shows a bluish-red shade when incorporated in plastics and paints.

EXAMPLE 13

A 500 ml flask equipped with a stirrer, thermometer, and condenser is charged with 16.4 grams of 45% aqueous potassium hydroxide, 15 ml water, and 130 ml DMSO. 10.7 grams 3,6-di(4-chlorphenyl)-1,4-diketopyrrolo[3,4-c]pyrrole crude and 10.2 grams 3,6-di-(4-methylphenyl)-1,4-diketopyrrolo-[3,4-c]-pyrrole crude are added, stirring at 40°–50° C. The mixture is heated to 70° C. and stirred at 70°–72° C. for five minutes. The resulting dark hot solution of the pigment salts is drowned into 1 liter of methanol at 20°30° C., causing the pigment to precipitate. The pigment suspension is refluxed for 1.5 hours then cooled to room temperature and filtered. The presscake is washed DMSO-free with methanol, followed with water to a pH 7–8 and dried. The red pulverized pigment solid solution shows an x-ray diffraction pattern which differs from the x-ray diffraction pattern of the corresponding physical mixture of the starting materials. Highly saturated, opaque bluish red colorations with excellent fastness to light, heat, and weathering are obtained when the product is incorporated into plastics.

Surprisingly, the pigment solid solution shows a much bluer shade in comparison with the corresponding mixtures of the starting materials.

EXAMPLE 14

The procedure of Example 13 is repeated using 16.1 grams of 3,6-di(4-chlorophenyl)-1,4-diketopyrrolo-[3,4,c]-pyrrole crude and 5.1 grams of 3,6-di(4-methylphenyl)-1,4-diketopyrrolo[3,4-c]pyrrole crude yielding a pigment solid solution with an x-ray diffraction pattern different from the x-ray diffraction pattern of the corresponding physical mixture of the starting materials. The x-ray diffraction pattern of this pigment solid solution also differs from the x-ray diffraction pattern of the pigment solid solution obtained according to Example 13. Very strong opaque bluish-red colorations with excellent fastness properties are obtained when incorporated in paints or plastics.

EXAMPLE 15

A 1 liter flask equipped with a stirrer, thermometer, and condenser is charged with 55.7 grams of 45% aqueous potassium hydroxide, 50 ml water, and 330 ml DMSO. 33.6 grams 3,6-di (4-chlorophenyl)-1,4-diketopyrrolo-[3,4-c]-pyrrole, 22.4 grams 3,6-diphenyl-1,4-diketopyrrolo-[3,4-c]-pyrrole and 14.0 grams 2,9-dimethylquinacridone are added with stirring at 40–50° C. The mixture is heated to 60°–65° C. and stirred for 5 minutes at 60°–65° C. The resulting hot black solution of the pigment salts is drowned into 1 liter of water at 20°–33° C., causing the pigment to precipitate. The pigment suspension is stirred for 2 hours at 28°–33° C. and filtered. The filtercake is washed with water to a pH 7–8.5 and dried. The red pulverized pigment shows a very strong yellowish-red color in TiO$_2$ extension and a highly transparent dark brownish-red masstone by rubout in a lithographic varnish systems obtained according to ASTM Method D-387-60.

The x-ray diffraction pattern of the ternary pigment solid solution differs completely from the x-ray diffraction pattern of the corresponding physical mixture of the starting materials. Despite the presence of the known strong magenta colored 2,9-dimethylquinacridone the pigment solid solution shows a saturated yellowish-red color in TiO$_2$ extension.

EXAMPLE 16

The procedure of Example 15 is repeated replacing 2,9-dimethylquinacridone with 2,9-dichloroquinacridone to yield a pigment solid solution with a similar x-ray diffraction pattern as the ternary pigment solid solution obtained in Example 15. The solid solution shows very strongly saturated yellowish-red colorations when applied in plastics and paints with excellent weathering properties.

EXAMPLE 17

A 500 ml flask equipped with a thermometer, stirrer, and condenser is charged with 16.4 grams of 45% aqueous potassium hydroxide, 13 ml water, and 120 ml DMSO. 24.0 grams 3,6-di(4-tert-butylphenyl)-1,4-diketopyrrolo[3,4-c] pyrrole crude are added, stirring at 40°–50° C. The mixture is heated to 50°–55° C. and stirred at 50°–55° C. for five minutes. The resulting solution is drowned into 550 ml of water at 20°–30° C., causing the pigment to precipitate. The pigment suspension is stirred for 1 hour at 25°–30° C. and filtered. The presscake is washed DMSO-free with water to a pH 7–8 and dried. The orange pulverized pigment shows a highly transparent, highly saturated orange masstone and a strong orange color in TiO$_2$ extension by rubout according to ASTM method D-387-60 in a lithographic varnish.

EXAMPLE 18

63.0 grams of polyvinylchloride, 3.0 grams epoxidized soya bean oil, 2.0 grams of barium/cadmium heat stabilizer, 32.0 grams dioctyl phthalate, and 1.0 gram of the pigment prepared according to Example 1 are mixed together in a glass beaker using a stirring rod. The mixture is formed into a soft PVC sheet with a thickness of about 0.4mm by rolling for 8 minutes on a two-roll laboratory mill at a temperature of 160° C., a roller speed of 25 RPM, and friction of 1:1.2 by constant folding, removal, and feeding. The resulting soft PVC sheet is colored in a high chroma attractive red shade with excellent fastness to heat, light, and migration.

EXAMPLE 19

5 grams of a pigment prepared according to Example 2, 2.5 grams hindered amine light stabilizer, 1.0 gram benzotriazole UV absorber, 1.0 gram hindered phenol antioxidant, and 1.0 gram phosphite process stabilizer are mixed in a Banbury mixer together with 1 kilogram of high density polyethylene at a speed of 175–200 RPM for 30 seconds after flux. The fluxed pigmented resin is chopped up while warm and malleable, and then fed through a granulator. The resulting granules are molded on a BATTENFELD 1000 injection molder with a 5-minute dwell time and a 30-second cycle time at temperatures of 205° C., 260° C., and 315° C., respectively. Homogenous colored chips showing a similar red color at each of the temperature steps are obtained.

EXAMPLE 20

The procedure of Example 19 is repeated using polypropylene instead of high density polyethylene as a substrate to yield red colored chips which show excellent heat and lightfastness properties.

EXAMPLE 21

Six grams of the DPP prepared according to Examples 1A and 1B are stirred into 20 grams of a mixture of the following composition: 50 grams of a mixture of aromatic hydrocarbons (SOLVESSO 150 from ESSO), 15 grams of butylacetate, 5 grams of ketoxime-based leveling agent, 25 grams of methyl isobutyl ketone, and 5 grams of silicone oil (1% in SOLVESSO 150). Upon complete dispersion, 48.3 grams of acrylic resin (51% in 3:1 xylene/butanol) and 23.7 grams of melamine resin are added, the batch is briefly homogenized in a horizontal bead mill under shear and the resultant coating composition sprayed onto a metal panel and stoved for 30 minutes at 130° C. The finish so obtained exhibits a high chroma red shade of excellent fastness properties, with the enamel being distinguished by good flow properties and excellent dispersion of the pigment.

EXAMPLE 22

The following ingredients are thoroughly milled for 64 hours in a ball mill:

| | |
|---|---|
| 25.2 grams | Polyester resin, 60% in SOLVESSO 150, |
| 2.7 grams | Melamine resin, 55% in butanol, |
| 15.5 grams | Cellulose acetobutyrate (25% in xylene/butyl acetate 1:2) |
| 1.1 grams | Catalyst based on mineral oil/carboxylate |
| 23.3 grams | Butyl acetate |
| 11.6 grams | Xylene |
| 1.6 grams | SOLVESSO 150 |
| 9.6 grams | Quinacridone/diketopyrrolo pyrrole solid solution obtained according to Example 11 |

The coating resulting from diluting the pigment dispersion with a mixture of butyl acetate/xylene/SOLVESSO 150 (in the same proportions as shown above) to a viscosity of about 18 seconds (20° C.) according to DIN 4, subsequent spraying onto a metal sheet, and exposure to air for 2 minutes at about 40° C. is further coated with a clear unpigmented topcoat. Exposure to air for 30 minutes at 40° C. and then stoving for 30 minutes at 135° C. yields a medium-shade red coating having excellent fastness properties.

EXAMPLE 23

This example illustrates the incorporation of a highly transparent DPP pigment prepared according to Example 7 in a mixture with a pearlescent mica pigment in an automotive coating finish:

Pigment Dispersion 80.0 grams Non-aqueous dispersion resin (NAD-resin), 17.6 grams dispersant-resin, 70.4 grams SOLVESSO 100 and 32.0 grams DPP pigment obtained according to Example 7 are ball milled for 64 hours. The dispersion contains 16.0% pigment and 48.0% solids at a pigment to binder ratio of 0.5.

Stabilized Resin Solution 144.6 grams of xylene, 90.0 grams methanol, 1353.0 grams NAD-resin, 786.2 grams melamine resin, 65.6 grams UV-screener solution, 471.6 grams acrylourethane resin, and 89.0 grams catalyst solution are mixed with an impeller stirrer in a gallon jar.

Mica Formulation 251.1 grams of pearlescent, titanium-dioxide-coated mica pigment, 315.0 grams NAD-resin, and 180.0 grams acrylourethane resin are mixed in a glass container. The mica formulation contains 27.9% mica pigment and 57.3% solids at a pigment to binder ratio of 0.5.

Paint Formulation (50 parts pigment/50 parts mica)

28.7 grams of the above described pigment dispersion, 16.5 grams of the above-described mica formulation, 61. grams acrylourethane resin, 3.5 grams NAD resin, and 70.2 grams of the above-described stabilized resin solution are mixed and sprayed onto a primed aluminum panel, followed by spraying a clearcoat resin onto the colored basecoat. The panel is exposed to ambient air for 10 minutes and stoved for 30 minutes at 130° C. A unique red-shade colored coating is obtained displaying an appearance of color depth and high flop with excellent weatherability.

EXAMPLE 23

Example 22 is repeated except that an equivalent amount of the pigment of Example 8 is used in place of the pigment of Example 7.

In addition to the embodiments described above, numerous variations of these embodiments can be made in accordance with this invention.

I claim:

1. A process for preparing a diaryldiketopyrrolo[3,4-c] pyrrole pigment, which comprises (a) preparing a pigment salt solution by dissolving a diaryldiketopyrrolo[3,4-c]pyrrole in dimethylsulfoxide which contains an effective salt-forming amount of a base and sufficient water to solubilize the base, (b) precipitating the diaryldiketopyrrolo[3,4-c] pyrrole from the pigment salt solution to form a pigment suspension, and (c) isolating the pigment.

2. A process of claim 1 wherein the base is an alkali metal hydroxide.

3. A process of claim 2 wherein the alkali metal hydroxide is sodium hydroxide or potassium hydroxide.

4. A process of claim 3 wherein the dimethylsulfoxide contains from 2 to 6 moles of the alkali metal hydroxide per mole of the diaryldiketopyrrolo[3,4-c]pyrrole.

5. A process of claim 4 wherein the concentration of the diaryldiketopyrrolo[3,4-c]pyrrole in the pigment salt solution is from about 8 to 17 percent by weight and temperature of the aqueous, basic dimethylsulfoxide is from about 50° C. to 80° C.

6. A process of claim 4 wherein the aqueous, basic dimethylsulfoxide contains 10 to 40 parts by weight of water per 100 parts of dimethylsulfoxide.

7. A process of claim 1 wherein the diaryldiketopyrrolo [3,4-c]pyrrole is precipitated from the pigment salt solution by drowning into water or a $C_1$–$C_4$alkanol, or a mixture thereof, in the presence or absence of a pigment particle growth inhibitor.

8. A process of claim 7 wherein the $C_1$–$C_4$alkanol is selected from the group consisting of methanol and ethanol.

9. A process of claim 7, which further comprises stirring the pigment suspension at a temperature of from 15° C. to 35° C. for a period of from 5 minutes to 10 hours prior to isolating the conditioned transparent pigment.

10. A process of claim 7 wherein the diaryldiketopyrrolo [3,4-c]pyrrole is selected from the group consisting of 3,6-di(4-chlorophenyl)-1,4-diketopyrrolo[3,4-c]pyrrole,3,6-di(4-tert-butylphenyl)-1,4-diketopyrrolo[3,4-c]pyrrole, 3,6-di( 3-cyanophenyl)-1,4-diketopyrrolo[3,4-c]-pyrrole, 3,6-di(4-biphenyl)-1,4-diketopyrrolo[3,4-c]pyrrole, 3,6-di(4-methylphenyl)-1,4-diketopyrrol 3,4-c]pyrrole and 3,6-diphenyl-1,4-diketopyrrolo[3,4-c]pyrrole.

11. A process of claim 1 wherein the pigment salt solution comprises the diaryldiketopyrrolo 3,4-c]pyrrole and a second dissolved organic pigment which forms a solid solution pigment with the diaryldiketopyrrolo[3,4-c]pyrrole upon precipitation.

12. A process of claim 11, wherein the second dissolved organic pigment is a different diaryldiketopyrrolo 3,4-c] pyrrole or a linear quinacridone.

13. A process of claim 11 wherein the base is an alkali metal hydroxide.

14. A process of claim 13 wherein the alkali metal hydroxide is sodium hydroxide or potassium hydroxide.

15. A process of claim 14 wherein the concentration of the pigment salts in the pigment salt solution is from about 8 to 17 percent by weight and temperature of the aqueous, basic dimethylsulfoxide is from about 50° C. to 80° C.

16. A process of claim 14 wherein the aqueous, basic dimethylsulfoxide contains 10 to 40 parts by weight of water per 100 parts of dimethylsulfoxide.

17. A process of claim 11 wherein the solid solution is precipitated from the pigment salt solution by drowning into water or a $C_1$–$C_4$alkanol, or a mixture thereof, in the presence or absence of a particle growth inhibitor.

18. A process of claim 17 wherein the $C_1$–$C_4$alkanol is selected from the group consisting of methanol and ethanol.

19. A process of claim 17, which further comprises stirring the solid solution pigment suspension at a temperature of from 15° C. to 35° C. for a period of from 5 minutes to 10 hours prior to isolating the transparent solid solution pigment.

20. A process of claim 11 wherein the solid solution pigment is a binary or ternary solid solution wherein the diaryldiketopyrrolo[3,4-c]pyrrole is selected from the group consisting of 3,6-di(4-chlorophenyl)-1,4-diketopyrrolo-[3,4-c]-pyrrole, 3,6-di(4-tert-butylphenyl)-1,4-diketopyrrolo [3,4-c]pyrrole, 3,6-di(3-cyanophenyl)-1,4-diketopyrrolo[3,4-c]pyrrole, 3,6-di(4-biphenyl)-1,4-diketopyrrolo-[3,4-c]-pyrrole, 3,6-di(4-methylphenyl)-1,4-diketopyrrolo-[3,4-c]-pyrrole, and 3,6-diphenyl-1,4-diketopyrrolo-[3,4-c]-pyrrole and the second pigment is one or two different pigments selected from the group consisting of 3,6-di(4-chlorophenyl)-1,4-diketopyrrolo[3,4-c]pyrrole, 3,6-di(4-tert-butylphenyl)-1,4-diketo- 3,4-c]pyrrole, 3,6-di(3-cyanophenyl)-1,4-diketopyrrolo[3,4-c]pyrrole, 3,6-di( 4-biphenyl)-1,4-diketopyrrolo[3,4-c]pyrrole, 3,6-di(4-methylphenyl)-1,4-diketo-pyrrolo[3,4-c]pyrrole, 3,6-diphenyl-1,4-diketopyrrolo[3,4-c]pyrrole, quinacridone, 2,9-dichloroquinacridone, 2,9-dimethoxyquinacridone and 2,9-dimethylquinacridone.

\* \* \* \* \*